United States Patent
Maruvada et al.

(10) Patent No.: US 8,795,406 B2
(45) Date of Patent: Aug. 5, 2014

(54) CROSS-LINKED POLYOLS FOR CONTROLLED RELEASE FERTILIZERS

(75) Inventors: Srirakrishna Maruvada, Birmingham, AL (US); Nick Peter Wynnyk, Edmonton (CA); Baozhong Xing, Loveland, CO (US)

(73) Assignee: Agrium Advanced Technologies (U.S.) Inc., Loveland, CO (US)

( * ) Notice: Subject to any disclaimer, the term of this patent is extended or adjusted under 35 U.S.C. 154(b) by 260 days.

(21) Appl. No.: 13/291,698

(22) Filed: Nov. 8, 2011

(65) Prior Publication Data
US 2012/0111077 A1    May 10, 2012

Related U.S. Application Data

(60) Provisional application No. 61/412,264, filed on Nov. 10, 2010.

(51) Int. Cl.
| | | |
|---|---|---|
| *C05D 9/00* | (2006.01) | |
| *C05D 9/02* | (2006.01) | |
| *C01C 1/18* | (2006.01) | |
| *A01N 25/00* | (2006.01) | |
| *C05G 3/00* | (2006.01) | |
| *C05C 9/00* | (2006.01) | |
| *C08G 18/36* | (2006.01) | |
| *C08G 18/38* | (2006.01) | |
| *C08G 75/04* | (2006.01) | |
| *C08G 75/26* | (2006.01) | |
| *C08G 75/00* | (2006.01) | |
| *C07C 327/22* | (2006.01) | |

(52) U.S. Cl.
CPC ............ *C05G 3/0029* (2013.01); *C05G 3/0035* (2013.01); *C05G 3/0023* (2013.01); *C05C 9/00* (2013.01); *C08G 18/36* (2013.01); *C08G 18/3868* (2013.01); *C08G 75/04* (2013.01); *C08G 75/26* (2013.01); *C08G 75/00* (2013.01); *C07C 327/22* (2013.01)
USPC .................................. 71/54; 71/31; 71/64.02

(58) Field of Classification Search
CPC .. C05G 3/0029; C05G 3/0035; C05G 3/0023; C05C 9/00; C08G 18/36; C08G 18/3868; C08G 75/04; C08G 75/26; C08G 75/00; C07C 327/22; C09D 175/04
USPC ........................................................ 71/23–49
See application file for complete search history.

(56) References Cited

U.S. PATENT DOCUMENTS

| | | |
|---|---|---|
| 4,711,659 A | 12/1987 | Moore |
| 4,804,403 A | 2/1989 | Moore |
| 5,213,723 A | 5/1993 | Aoshima et al. |
| 5,374,292 A | 12/1994 | Detrick |
| 5,538,531 A | 7/1996 | Hudson |
| 5,599,374 A | 2/1997 | Detrick |
| 5,851,261 A | 12/1998 | Markusch et al. |
| 6,039,781 A | 3/2000 | Goertz et al. |
| 6,152,981 A | 11/2000 | Markusch et al. |
| 6,176,891 B1 | 1/2001 | Komoriya et al. |
| 6,231,633 B1 | 5/2001 | Hirano et al. |
| 6,338,746 B1 | 1/2002 | Detrick et al. |
| 6,358,296 B1 | 3/2002 | Markusch et al. |
| 6,364,925 B1 | 4/2002 | Markusch et al. |
| 6,663,686 B1 | 12/2003 | Geiger et al. |
| 7,713,326 B2 * | 5/2010 | Carstens et al. ................. 71/28 |
| 7,771,505 B2 | 8/2010 | Ogle et al. |
| 2006/0111520 A1 | 5/2006 | Byers et al. |
| 2010/0307211 A1 * | 12/2010 | Xing et al. ........................ 71/27 |
| 2012/0111076 A1 * | 5/2012 | Avdala et al. .................... 71/27 |
| 2012/0111077 A1 * | 5/2012 | Maruvada et al. ............... 71/27 |

FOREIGN PATENT DOCUMENTS

| | | |
|---|---|---|
| DE | 10 2008 000 595 | 9/2009 |
| WO | 2005/080325 | 9/2005 |
| WO | 2008/106637 | 9/2008 |

OTHER PUBLICATIONS

Schuchardt et al., "Transesterification of Vegetable Oils: a Review," J. Braz. Chem. Soc., vol. 9, No. 1, 199-210, 1998.
International Search Report and Written Opinion, International Application No. PCT/US2011/059766, mailed Dec. 4, 2012.

* cited by examiner

*Primary Examiner* — Jennifer A Smith
(74) *Attorney, Agent, or Firm* — Kagan Binder, PLLC

(57) ABSTRACT

A controlled release fertilizer material comprising a particulate plant nutrient surrounded by a coating including a mixture of a cross-linked polyol and an isocyanate, and optionally a wax, is described. In some embodiments, the cross-linked polyol can be cross-linked with sulfur, oxygen, and/or a peroxide cross-linking moiety. In one embodiment the cross-linked polyol is castor oil cross-linked with sulfur.

7 Claims, No Drawings

CROSS-LINKED POLYOLS FOR CONTROLLED RELEASE FERTILIZERS

CROSS REFERENCE TO RELATED APPLICATIONS

This application claims the benefit of U.S. Provisional application No. 61/412,264 filed Nov. 10, 2010 entitled "CROSS-LINKED POLYOLS FOR CONTROLLED RELEASE FERTILIZERS", the entire disclosure of which is incorporated herein.

The present invention relates to controlled release fertilizers such as those disclosed in U.S. Pat. No. 7,771,505 and U.S. Pat. No. 6,663,686, both of which are incorporated herein by reference in their entirety for all purposes. Additionally, the present application is related to the following co-owned and co-pending applications: U.S. Ser. No. 13/291,681 which claims priority to U.S. Provisional application No. 61/412,251 entitled CONTROLLED RELEASE FERTILIZERS MADE FROM CROSS-LINKED GLYCERIDE MIXTURES, and U.S. Ser. No. 13/291,663 which claims priority to U.S. Provisional application No. 61/412,246 entitled CROSS-LINKED MODIFIED WAXES FOR CONTROLLED RELEASE FERTILIZERS, both filed on even date herewith, and all of which are incorporated hereby by reference in their entireties for all purposes.

TECHNICAL FIELD

The present invention relates to controlled release fertilizers. More particularly, the present invention relates to a controlled release fertilizer material comprising a particulate plant nutrient surrounded by a coating.

BACKGROUND

Fertilizers have been used for many years to supplement nutrients in growing media. In recent years the art has focused on techniques to deliver controlled amounts of plant nutrients to the soil or other growing media. It is recognized, for example, that controlling the release of plant nutrients such as nitrogen from highly soluble fertilizer granules is desirable because releasing the nutrients over an extended period of time achieves advantages which include increased efficiency of fertilizer use by plants, reduced application costs since fewer applications of fertilizer are required and reduced nutrient loss caused by leaching and denitrification.

U.S. Pat. No. 5,538,531 (Hudson) teaches a controlled release, particulate fertilizer product having a water soluble fertilizer central mass encased in a plurality of water insoluble, abrasion resistant coatings. At least one inner coating is a urethane reaction product derived from reacting recited isocyanates and polyols. The outer coating is formed from an organic wax.

U.S. Pat. No. 6,358,296 (Markusch et al.) teaches a slow-release polyurethane encapsulated fertilizer using oleo polyol(s). U.S. Pat. No. 5,851,261 (Markusch et al.) provides a process for the production of polyurea encapsulated fertilizer particles comprising applying an isocyanate-reactive component containing at least two amine groups to the fertilizer particles, and applying a polyisocyanate to the amine coated particles to form polyurea coated particles.

Sulfur containing isocyanate compositions and a process for the production of encapsulated fertilizer compositions are described in U.S. Pat. No. 6,152,981 (Markusch et al.). The fertilizer compositions are prepared by applying a mixture of sulfur and an isocyanate to the fertilizer and then applying an isocyanate-reactive material. U.S. Pat. No. 5,599,374 (Detrick) describes a fertilizer composition wherein a sulfur coating is applied to a fertilizer core, and thereafter a polymer coating is applied over the sulfur.

U.S. Pat. No. 6,231,633 (Hirano et al.) teaches a granular fertilizer coated with a thermosetting resin coating that may be urethane and a hydrophobic compound, which may be wax. U.S. Pat. No. 6,663,686 (Geiger et al.) teaches a slow-release polyurethane encapsulated fertilizer using polyurethane and wax.

U.S. Pat. No. 6,039,781 (Goertz et al.) teaches that it is also known in the art to pre-coat particulate plant nutrient with organic oil and particles as a means to improve the release profiles of the particulate plant nutrient.

U.S. Pat. No. 6,338,746 (Detrick et al.) describes a process of first coating a fertilizer with a polymer, then coating the polymer with sulfur and thereafter applying a polymer coating. The polymers are described in U.S. Pat. No. 4,711,659 (Moore), U.S. Pat. No. 4,804,403 (Moore) and U.S. Pat. No. 5,374,292 (Detrick). These polymers require that the substrate contains a minimum quantity of reactive —$NH_2$ groups. Thus, these are not applicable to all fertilizer compositions for which slow release properties may be desirable.

U.S. Pub. No. 2010/0307211 describes a controlled release fertilizer comprising at least one coating that includes a reaction product of a polyol, an isocyanate, a wax and an epoxidized fatty acid triglyceride oil.

Although polymer coated fertilizers as above described have received substantial attention, they are expensive to manufacture. There is a need in the art to provide controlled released fertilizer formulations that are abrasion resistant, and that reduce the cost of fertilizer production. Additionally, it would be desirable to have a controlled release fertilizer and process for production thereof which would allow for the ready customization of the release rate profile of a given particulate plant nutrient having applied thereto a given amount of urethane coating(s). It would also be desirable to be able to achieve a desirable release rate profile for a given particulate plant nutrient using significantly reduced amounts of coating materials.

SUMMARY

According to various embodiments, the present invention is a controlled release fertilizer composition including a plant nutrient coated with a reaction product of a mixture including an isocyanate and at least one modified polyol, wherein the modified polyol is cross-linked with sulfur, oxygen and/or a peroxide cross-linking moiety or alternatively, wherein the polyol is cross-linked at unsaturated sites in the modified polyol using heat, UV or ionizing radiation.

In some embodiments, the modified polyol includes castor oil, vegetable oil derived polyols, or glycerides. In other embodiments, the modified polyol includes a mixture of monoglycerides and/or diglycerides formed by reacting a triglyceride and/or diglyceride with a hydroxyl containing compound. In still other embodiments, the modified polyol is the reaction product of glycerol and one or more triglycerides reacted in the presence of a catalyst.

In certain embodiments, the coating further comprises an unsaturated wax. The unsaturated wax can be one or more vegetable oils, glycerides, fatty acids, olefin waxes, silicone waxes, oxidized waxes, natural waxes, natural oils, partially hydrogenated oils, or fats.

In other embodiments, the present invention is a method of producing a controlled release fertilizer containing a cross-linked polyol.

While multiple embodiments are disclosed, still other embodiments of the present invention will become apparent to those skilled in the art from the following detailed description, which shows and describes illustrative embodiments of the invention. Accordingly, the detailed description is to be regarded as illustrative in nature and not restrictive.

DETAILED DESCRIPTION

Controlled release fertilizers containing a cross-linked polyol may demonstrate a more controlled release rate when compared to controlled release fertilizers of similar composition containing the same polyol that is not cross-linked.

According to various embodiments, the present invention is a controlled release fertilizer composition including a plant nutrient coated with a reaction product of a mixture including an isocyanate, a wax, and a modified polyol which is a reaction product of glycerol and a triglyceride, wherein the modified polyol is cross-linked with sulfur, oxygen and/or a peroxide cross-linking moiety.

In some embodiments, the present invention is a controlled release fertilizer including a polyurethane coated plant nutrient in which the polyurethane includes a polyol monomer component having the following formula:

X—CH$_2$—CH(OH)—CH$_2$OH wherein X is —O—CO—C$_y$H$_z$, wherein y ranges from 15-21 and z ranges from 29-41. The polyol may be cross-linked with either sulfur, oxygen and/or a peroxide cross-linking moiety or alternatively, the polyol may be cross-linked at unsaturated sites in the polyol using heat, UV, or ionizing radiation. In one embodiment, y is 15-17 and z is 29-33. In a further embodiment, the polyurethane may further include a diglyceride polyol monomer component.

Plant Nutrient Material

The choice of particulate plant nutrient material useful for the present controlled release fertilizer material is not to be restricted. The present fertilizer material has been described primarily with reference to urea as the plant nutrient. As will be apparent to one skilled in the art, however, other nutrients, including primary nutrients, secondary nutrients and micronutrients, can be used to prepare the controlled release fertilizer compositions in accordance with the present invention. Typically, the plant nutrient material is provided in the form of a water soluble particulate material. The plant nutrient present within the controlled release fertilizer according to the various embodiments of the present invention, as described herein, can include primary nutrients such as urea, ammonium nitrate, potassium nitrate, ammonium phosphates and other suitable nitrogen derivatives; potassium phosphates and other suitable phosphorus derivatives; and potassium nitrate, potassium sulfate, potassium chloride and other suitable potassium derivatives as well as mixtures of these primary nutrients. Additionally, the plant nutrient can include a suitable secondary nutrients and micronutrients. Suitable micronutrients include, but are not limited to iron sulfates, copper sulfate, manganese sulfate, zinc sulfate, boric acid, sodium molybdate and its derivatives, magnesium sulfate, potassium/magnesium sulfate, and derivatives and mixtures thereof.

Urea is characterized as having functional reactive groups at the surface of the urea which may be used to react with a diisocyanate when forming the polymer layer. This reaction causes the polymer layer to be chemically bonded to the urea. However, according to the present invention, it is not required that the polymer layer be bonded to the urea material.

The amounts of nutrients present within the controlled release fertilizer composition as describe herein may vary as follows, where the listed amounts are weight percentages based on the weight of the fertilizer composition:
Nitrogen derivatives (as Nitrogen): 0 wt. %-45.54 wt. %
Phosphorus derivatives (as P$_2$O$_5$): 0 wt. %-51.48 wt. %
Potassium derivatives (as K$_2$O): 0 wt. %-61.38 wt. %
Iron Sulfate: 0 wt. %-99 wt. %
Iron EDTA chelate: 0 wt. %-99 wt. %
Copper Sulfate: 0 wt. %-99 wt. %
Manganese Sulfate: 0 wt. %-99 wt. %
Zinc Sulfate: 0 wt. %-99 wt. %
Sodium Molybdate: 0 wt. %-99 wt. %
Sodium Borate: 0 wt. %-99 wt. %, and/or
Magnesium Sulfate: 0 wt. %-99 wt. %.

In some embodiments, the coating surrounds the plant nutrient core in an amount ranging from about 1.0 to about 20 wt. %, more particularly from about 1.5 to about 5.0 wt. %, and most particularly from about 2.0 to about 4.0 wt. %, based on the weight of the plant nutrient material.

Isocyanate

The isocyanate used to produce the coating according to the various embodiments of the present invention is not to be restricted. Isocyanates contain two or more —NCO groups available for reaction and, as known to one skilled in the art, are widely, used in the production of urethane polymers. Generally, the isocyanate compound suitable for use may be represented by the general formula:

Q(NCO)$_i$ wherein i is an integer of 2 or more and Q is an organic radical having the valence of i. Q may be a substituted or unsubstituted hydrocarbon group (e.g. an alkylene or arylene group). Moreover, Q may be represented by the general formula:

Q$^1$-Z-Q$^1$ wherein Q$^1$ is an alkylene or arylene group and Z is chosen from the group comprising —O—, —O-Q$^1$-, —CO—, —S—, —S-Q$^1$-S— and SO$_2$—. Examples of isocyanate compounds which fall within the scope of this definition include hexamethylene diisocyanate, 1,8-diisocyanato-p-methane, xylyl diisocyanate, (OCNCH$_2$CH$_2$CH$_2$OCH$_2$O)$_2$, 1-methyl-2,4-diisocyanatocyclohexane, phenylene diisocyanates, tolylene diisocyanates, chlorophenylene diisocyanates, diphenylmethane-4,4'-diisocyanate, naphthalene-1,5-diisocyanate, triphenylmethane-4,4',4"-triisocyanate and isopropylbenzene-alpha-4-diisocyanate.

In another embodiment, Q may also represent a polyurethane radical having a valence of i. In this case Q(NCO)$_i$ is a compound which is commonly referred to in the art as a prepolymer. Generally, a prepolymer may be prepared by reacting a stoichiometric excess of an isocyanate compound with an active hydrogen-containing compound such as, for example, the polyhydroxyl-containing materials or polyols, as they are commonly referred to, discussed below. In this embodiment, the polyisocyanate may be, for example, used in proportions of from about 30 percent to about 200 percent stoichiometric excess with respect to the proportion of hydroxyl in the polyol.

In another embodiment, the isocyanate compound suitable for use in the process of the present invention may be selected from dimers and trimers of isocyanates and diisocyanates, and from polymeric diisocyanates having the general formula:

[Q'(NCO)$_i$]$_j$ wherein both i and j are integers having a value of 2 or more, and Q' is a polyfunctional organic radical, and/or, as additional components in the reaction mixture, compounds having the general formula:

wherein i is an integer having a value of 1 or more and L is a monofunctional or polyfunctional atom or radical. Examples of isocyanate compounds which fall with the scope of this definition include ethylphosphonic diisocyanate, phenylphosphonic diisocyanate, compounds which contain a =Si—NCO group, isocyanate compounds derived from sulphonamides (QSO$_2$NCO), cyanic acid and thiocyanic acid.

Additional non-limiting examples of suitable isocyanates include: 1,6-hexamethylene diisocyanate, 1,4-butylene diisocyanate, furfurylidene diisocyanate, 2,4-toluene diisocyanate (TDI), 2,6-toluene diisocyanate (2,6-TDI), 2,4'-diphenylmethane diisocyanate, 4,4'-diphenylmethane diisocyanate (MDI), 4,4'-diphenylpropane diisocyanate, 4,4'-diphenyl-3,3'-dimethyl methane diisocyanate, 1,5-naphthalenediisocyanate, 1-methyl-2,4-diisocyanate-5-chlorobenzene, 2,4-diisocyanato-s-triazine, 1-methyl-2,4-diisocyanato cyclohexane, p-phenylene diisocyanate, m-phenylene diisocyanate, 1,4-naphthalene diisocyanate, dianisidine diisocyanate, bitoluene diisocyanate, 1,4-xylylene diisocyanate, 1,3-xylylene diisocyanate, bis-(4-isocyanatophenyl)methane, bis-(3-methyl-4-isocyanatophenyl)methane, polymethylene polyphenyl polyisocyanates and mixtures thereof. In one embodiment, the isocyanate used to produce the coating is 2,4-toluene diisocyanate (TDI). In another embodiment, the isocyanate used to produce the coating is 4,4'-diphenylmethane diisocyanate (MDI). Other suitable isocyanates are described in U.S. Pat. No. 6,364,925 (Markusch et al.), which is incorporated herein by reference in its entirety for all purposes. In some embodiments, the isocyanate can be an isomeric, oligomeric, monomeric, or polymeric form of a diphenylmethane diisocyanate or a toluene diisocyanate.

Preferably, the polyol and isocyanate are used in amounts such that the ratio of NCO groups in the isocyanate to the hydroxyl groups in the polyol ranges from about 0.8 to about 3.0, more particularly from about 0.8 to about 2.0, and most particularly from about 0.8 to about 1.5.

Modified Polyols and Polyhydroxyl Compounds

A polyhydroxyl compound is a compound containing two or more hydroxyl groups available for reaction and includes those compounds typically referred to as polyols.

A modified polyol is a polyol that has been cross-linked. More particularly, a modified polyol is a polyol that has been cross-linked with another compound (including itself) at an unsaturated site within the compound. According to the various embodiments of the present invention, the modified polyol can be cross-linked with itself, with a triglyceride or with an unsaturated wax. In some embodiments, the modified polyol can be cross-linked with both an unsaturated wax and a triglyceride, or with an unsaturated wax and a triglyceride derivative, or with an unsaturated wax and mixtures of one or several triglycerides and/or one or several triglyceride derivatives.

A triglyceride derivative is any product of one or more simultaneous, or sequential chemical reactions of any one, or a combination of, triglycerides, diglycerides, monoglycerides, fatty acids, glycerol and their respective reaction products including, but not limited to, epoxidized glycerides, glycerides where epoxy groups are further converted to hydroxyl and/or ester groups, glycerides partially, or fully hydrogenated, and/or oxidized, cooked, or bodied and/or ozonized and/or hydrolyzed and/or transesterified, and/or cross-linked, dimerized, or polymerized and glycerides having undergone other addition and/or substitution reactions.

Additionally, in some examples, the modified polyol can include two or more polyhydroxyl compounds that are cross-linked at an unsaturated site within each of the compounds. In certain embodiments, the modified polyol is a castor oil that has been cross-linked according to the different embodiments described above.

The choice of polyol is not particularly restricted. The polyol may be any hydroxyl-containing compound, or a mixture of different hydroxyl-containing compounds including, but not limited to polyether, polyester, epoxy, polycarbonate, polydiene or polycaprolactone. In some embodiments, the polyol compound is used as a modifier in the reaction mixture, in which case, for the purposes of this application, it is then referred to as a polyhydroxyl compound.

Non-limiting examples of polyhydroxyl compounds and polyols suitable for use in the controlled released fertilizers according to the various embodiments of the present invention include hydroxyl-terminated polyhydrocarbons, hydroxyl-terminated polyformals, fatty acid triglycerides, hydroxyl-terminated polyesters, hydroxymethyl-terminated polyesters, hydroxymethyl-terminated perfluoromethylenes, polyalkyleneether glycols, polyalkylenearyleneether glycols and polyalkyleneether triols. Additional non-limiting examples of suitable polyols are those described in U.S. Pat. No. 4,804,403 to Moore (see, for example; column 9, lines 3-20, and example 1), which is incorporated herein by reference in its entirety for all purposes. Further non limiting examples of polyhydroxyl compounds and polyols suitable for use in the various embodiments of the present invention include diethylene glycol polyol, ethylene glycol, polypropylene glycol, organic polyols, for example as described in U.S. Pat. No. 4,804,403 to Moore, orthophathalate diethylene glycol based polyester polyols, terephthalate-diethylene glycol based polyester polyols, castor oil and oils modified to contain amine or hydroxyl groups, for example modified tung oil, soybean oil, canola oil, sunflower oil, linseed oil, e.g. U.S. Pat. No. 6,364,925 to Markusch et al. (see, for example column 8 line 39 to column 9, line 27 and the examples) and U.S. Pat. No. 6,358,296 to Markusch et al. (see, for example column 9 lines 1 to 13, and the examples; which are all incorporated herein by reference in their entireties for all purposes), oleo-polyols, for example an epoxidized castor oil, epoxidized sunflower oil, epoxidized linseed oil as described in U.S. Pat. No. 6,358,296 to Markusch et al. (which is incorporated herein by reference in its entirety for all purposes), polyether polyols, castor oil derivatives for example partial hydrolysates of castor oil, by, reacting castor oil with a polyol selected from diols (e.g. ethylene glycol, propylene glycol, 1,4-butanediol, neopentyl glycol, 1,6-hexanediol, diethylene glycol, dipropylene glycol, polyethylene glycol, and polypropylene glycol), glycerol, trimethylolpropane, and polyether polyol, or esters formed by reactions between ricinoleic acid and the polyol selected from these compounds as described in U.S. Pat. No. 6,176,891 to Komoriya et al. (see, for example column 7 lines 4 to 16, column 8, lines 49 to 62; which is incorporated herein by reference in its entirety for all purposes), or combinations thereof.

Additionally, the polyhydroxyl compound or polyol may be derived from natural sources such as soybean, corn, canola, sunflower, safflower, and the like. Vegetable oil derived polyols are also sometimes referred to as oleo polyols or triglycerides. According to some embodiments of the present invention, the polyol is an oleo polyol. In some embodiments, the polyol includes reaction products of glycerol and vegetable oils and/or animal fats including soybean oil, sunflower oil, canola oil, corn oil, safflower oil, tall oil, tallow, lard and mixtures thereof.

In other embodiments of the invention, the polyol is a mixture of monoglycerides and/or diglycerides formed by reacting a triglyceride and/or a diglyceride with any aliphatic, or aromatic, saturated, or unsaturated, natural, or synthetic, liquid, or solid, monofunctional, difunctional, trifunctional, or polyfunctional hydroxyl compound including, but not limited to: methanol, ethanol, propanol, isopropanol, butanol, isobutanol, pentanol, propenol, propynol, butane diol, butenediol, butynediol, ethylene glycol, diethylene glycol, triethylene glycol, propanediol, dipropylene glycol, polyethylene glycol, polypropylene glycol, trimethylol propane, pentaerythritol, caprolactone polyols, carbonate polyols, ethanolamine, diethanolamine, triethanolamine, tetra (2-hydroxypropyl)ethylenediamine, sorbitol, simple and/or complex sugars and the like.

In certain embodiments, the polyol used in the present invention is a mixture of cross-linked mono- and/or diglycerides having a normalized viscosity in a range of 1-50, where the normalized viscosity is determined as a ratio of the measured viscosity of the cross-linked mixture over the measured viscosity of the uncross-linked mixture.

According to some embodiments of the present invention the polyhydroxyl compound or polyol is a catalytic reaction product of glycerol and triglycerides and is cross-linked with sulfur. A variety of catalytic reagents can be used to catalyze the reaction between the glycerol and the triglyceride to produce a glyceride mixture. Suitable catalysts include acids, bases, organic, inorganic or biologically active compounds, examples of which include, but are not limited to the following: strong bases such as sodium hydroxide, strong acids such as sulfuric and sulfonic acids, p-toluene sulfonic acid, metal alkoxides, aluminum isopropoxide, tetraalkoxytitanium compounds such as tetraisopropyl titanate, organotin alkoxides, lithium ricinoleate, zinc acetate, sodium carbonate, potassium carbonate, hydrolytic enzymes such as lipase, non-ionic base catalysts such as amines, guanidines and many others listed in an article entitled "Transesterification of Vegetable Oils: a Review" by Ulf Schuchardt et al., J. Braz. Chem. Soc., Vol. 9, No. 1, 199-210, 1998, which is incorporated herein by reference in its entirety for all purposes.

According to other embodiments of the present invention, the polyhydroxyl compound or polyol is a catalytic reaction product of glycerol and triglycerides and is cross-linked with an oxygen containing or peroxide cross-linking moiety. U.S. Pat. No. 5,213,723 to Aoshima et al., which is incorporated herein by reference in its entirety, for all purposes, provides a list of peroxide cross-linking agents suitable for use with the various embodiments of the present invention as described herein. Exemplary suitable peroxide cross-linking agents include, but are not limited to, the following benzoyl peroxide, 2,4, dichlorobenzoyl peroxide, dicumyl peroxide, 1,3-bis(t-butylperoxyisopropyl)benzene, 2,5-dimethyl-2,5-di(t-butylperoxy)hexane, 1,1-di-t-butylperoxy-3,3,5-trimethylcyclohexane, cumene hydroperoxide, di-t-butyl peroxide, t-butylcumyl peroxide, p-chlorobenzoyl peroxide, t-butyl peroxybenzoate, and t-butylperoxyisopropyl carbonate.

Wax

The wax used to produce the coating according to the various embodiments of the present invention may be a single type of wax or a mixture of different waxes. For example, the wax may be selected from an intermediate petroleum wax, an alpha olefin wax, a polyethylene wax, a paraffin wax, a silicone wax, a slack wax, a microcrystalline wax, a natural wax, a natural oil or a fat. In some embodiments, the wax is an oxidized or "cooked" wax. Non-limiting examples of waxes that may be used in the compositions of the controlled release fertilizer of the present invention include those described in U.S. Pat. No. 5,538,531 to Hudson (see, for example column 5, lines 13 to 27 and the examples; which is incorporated herein by reference in its entirety for all purposes). The wax may comprise a drop melting point temperature of between about 60° C. and 90° C., or any temperature therebetween, for example 60, 62, 64, 66, 68, 70, 72, 74, 76, 78, 80, 82, 84, 86, 88, 90° C. In certain embodiments, the wax is a $C_{30+}$ alpha olefin wax. Suitable representative waxes and their melting points are listed in the table below.

| Wax Type | Melting Point (° C.) |
|---|---|
| $C_{30+}$ wax (100%) | 64.0 |
| $C_{30+}$ wax (95%) x-linked with 5% sulfur | 68.5 |
| $C_{30+}$ wax (80%) x-linked with castor oil (10%) and sulfur (10%) | 66.8 |
| $C_{30+}$ wax (80%) x-linked with Soybean oil (10%) and sulfur (10%) | 62.0 |
| $C_{30+}$ wax (80%) x-linked with canola oil glycerides (10%) and sulfur (10%) | 66.3 |
| $C_{30+}$ wax (80%) x-linked with Soybean oil (10%) and sulfur (10%) | 62.0 |
| Partially hydrogenated castor oil (95%) x-linked with 5% sulfur | 89.8 |
| Partially hydrogenated Soybean oil (95%) x-linked with 5% sulfur | 54.2 |

In some embodiments, the wax is an alpha olefin wax. In some embodiments, the wax is a $C_{22}$-$C_{35}$ alpha olefin wax. In certain embodiments, the wax is a $C_{30+}$ alpha olefin wax. In still certain other embodiments, the wax is a cross-linked alpha-olefin wax. In one embodiment, the wax is a cross-linked $C_{30+}$ alpha olefin wax. The cross-linked alpha olefin wax can be cross-linked with either sulfur or an oxygen containing or peroxide cross-linking moiety. U.S. Pat. No. 5,213,723, which is incorporated herein by reference in its entirety for all purposes, provides a list of peroxide cross-linking agents suitable for use with the various embodiments of the present invention as described herein. Exemplary suitable peroxide cross-linking agents include, but are not limited to, the following benzoyl peroxide, 2,4, dichlorobenzoyl peroxide, dicumyl peroxide, 1,3-bis(t-butylperoxyisopropyl)benzene, 2,5-dimethyl-2,5-di(t-butylperoxy)hexane, 1,1-di-t-butylperoxy-3,3,5-trimethylcyclohexane, cumene hydroperoxide, di-t-butyl peroxide, t-butylcumyl peroxide, p-chlorobenzoyl peroxide, t-butyl peroxybenzoate, and t-butylperoxyisopropyl carbonate.

In some embodiments, an alpha olefin wax is pre-mixed with a polyhydroxyl compound to produce a mixture or combination that is then cross-linked. In one embodiment, the polyhydroxyl compound is castor oil. The mixture can then be cross-linked with sulfur or an oxygen containing or peroxide cross-linking moiety.

According to various embodiments, the wax is present in the mixture in an amount of up to about 50 wt. %, based on the combined weight of the wax and the polyol. More particularly, the wax is present in the mixture in an amount in the range of from about 1.0 to about 25 wt. %, based on the combined weight of the wax and the polyhydroxyl compound. Most particularly, the wax is present in the mixture in an amount in the range of from about 2.0 to about 10 wt. % based, on the combined weight of the wax and the polyhydroxyl compound.

A process for producing the controlled release fertilizers according to the various embodiments of the present invention, as described above, will now be described. In one embodiment, the process includes the step of contacting glycerol with a triglyceride such as, for example, one of the triglycerides described above in the presence of a catalyst to produce a polyol. The polyol is then contacted with a cross-linking agent to provide a cross-linked polyol. In a further step, a particulate plant nutrient is contacted with a mixture including the cross-linked polyol, an isocyanate and a wax to provide a coated particulate plant nutrient followed by curing the coated particulate plant nutrient to provide a controlled release fertilizer.

In one embodiment, the process includes contacting glycerol with a triglyceride in the presence of a catalyst to provide a polyol having the following formula:

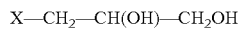

wherein X is —O—CO—$C_yH_z$, wherein y ranges from 15-21 and z is ranges from 29-41. The polyol may be cross-linked with either sulfur, oxygen and/or a peroxide cross-linking moiety. In one embodiment, y is 15-17 and z is 29-33. In a further embodiment, the polyurethane may further include a diglyceride polyol monomer component.

The precise mode of applying the mixture including the cross-linked polyol, isocyanate and wax to the plant nutrient is not particularly restricted. In some embodiments, the step of applying the mixture to the particulate plant nutrient includes contacting the particulate plant nutrient with a first stream comprising the cross-linked polyol and a second stream comprising the isocyanate, the first stream and the second stream being independent of one another. In one embodiment, the first stream can include a mixture of the cross-linked polyol and the wax. In this embodiment, the particulate plant nutrient may be contacted simultaneously with the first stream and the second stream. In another embodiment, the particulate plant nutrient is initially contacted with the first stream followed by the second stream. In still other embodiments, the coating process is repeated at least once to produce a controlled release fertilizer material having a plurality of coating layers.

In still other embodiments of manufacturing a controlled release fertilizer, urea granules of known weight are charged into a rotary drum reactor. Chemicals needed for certain target coating weight are measured and kept ready. The coating process includes the step of heating the urea in the rotating drum reactor to a target temperature (typically anywhere from 50° C. to 90° C.) followed by multiple chemical applications. The time delay between the chemical applications, also referred to as layer timing, is typically kept constant. The first layer includes triethanolamine (TEA) and MDI. The second, third and fourth layers are identical, and are made up of the reaction product of a polyol mixture and MDI. Before the fourth layer, a small amount of slightly oxidized wax is added to prevent caking or agglomeration. The polyol mixture used in the second, third and fourth layers can include a polyol, QUADROL polyol as the catalyst, and $C_{30+}$HA alpha-olefin wax. The catalyst and wax each make up about 5 wt. % of the mixture, with the remainder being the polyol. During the application of chemicals, the rotary drum reactor is kept at a constant temperature using a hot air blower. Once all the chemicals are applied and reaction is complete, then heat is turned off and the rotating bed of urea granules is allowed to cool to ambient temperature.

According to the embodiments of the present invention, the composition of the polyol mixture is a variable. Since this mixture contains three components, only one of the three such as, for example, the type of polyol used, is varied. Glyceride mixtures obtained from soybean oil, canola oil and sunflower can be used as polyol candidates. The glyceride mixtures can also be cross-linked with sulfur (up to 25 wt. %) and used as polyol candidates in accordance with various embodiments of the present invention.

Selected Particular Embodiments

One particular embodiment of this disclosure is a controlled release fertilizer composition that has a plant nutrient coated with a coating comprising an isocyanate and a modified polyol, wherein the modified polyol comprises at least one cross-linked polyhydroxyl compound. The modified polyol may include castor oil, vegetable oil derived polyols, glyceride mixtures, or unsaturated oleo polyols, or alternately or additionally a mixture of monoglycerides and/or diglycerides formed by reacting a triglyceride and/or a diglyceride with any aliphatic or aromatic, saturated or unsaturated, natural or synthetic, liquid or solid, monofunctional, difunctional, trifunctional or polyfunctional hydroxyl compound comprising methanol, ethanol, propanol, isopropanol, butanol, isobutanol, pentanol, propenol, propynol, butane diol, butenediol, butynediol, ethylene glycol, diethylene glycol, triethylene glycol, propanediol, dipropylene glycol, polyethylene glycol, polypropylene glycol, trimethylol propane, pentaerythritol, caprolactone polyols, carbonate polyols, ethanolamine, diethanolamine, triethanolamine, tetra (2-hydroxypropyl) ethylenediamine, sorbitol, or simple and/or complex sugars. The modified polyol can be the reaction product of glycerol and the one or more triglycerides reacted in the presence of a catalyst, wherein the catalyst comprises acids, bases organic, inorganic or biologically active compounds including, but not limited to sodium hydroxide, sulfuric acid, sulfonic acid, p-toluene sulfonic acid, metal alkoxides, aluminum isopropoxide, tetraisopropyl titanate, organotin alkoxides, lithium ricinoleate, zinc acetate, sodium carbonate, potassium carbonate, lipase, amines, or guanidines. The plant nutrient may be particulate.

Another particular embodiment of this disclosure is a controlled release fertilizer composition comprising a particulate plant nutrient coated with a coating comprising an isocyanate and a modified polyol, wherein the modified polyol comprises at least one polyhydroxyl compound cross-linked with an unsaturated triglyceride or triglyceride derivative. In some embodiments the modified polyol includes castor oil, vegetable oil based polyols, fatty acids, glyceride mixtures, or unsaturated oleo polyols. In other embodiments, the modified polyol includes a mixture of monoglycerides and/or diglycerides formed by reacting a triglyceride and/or diglyceride with any aliphatic or aromatic, saturated or unsaturated, natural or synthetic, liquid or solid, monofunctional, difunctional, trifunctional or polyfunctional hydroxyl compound comprising methanol, ethanol, propanol, isopropanol, butanol, isobutanol, pentanol, propenol, propynol, butane diol, butenediol, butynediol, ethylene glycol, diethylene glycol, triethylene glycol, propanediol, dipropylene glycol, polyethylene glycol, polypropylene glycol, trimethylol propane, pentaerythritol, caprolactone polyols, carbonate polyols, ethanolamine, diethanolamine, triethanolamine, tetra (2-hydroxypropyl) ethylenediamine, sorbitol, or simple and/or complex sugars. The modified polyol can be the reaction product of glycerol and the one or more triglycerides reacted in the presence of a catalyst, wherein the catalyst comprises acids, bases organic, inorganic or biologically active compounds including, but not limited to sodium hydroxide, sulfuric acid, sulfonic acid, p-toluene sulfonic acid, metal alkoxides, aluminum isopropoxide, tetraisopropyl titanate, organotin alkoxides, lithium ricinoleate, zinc acetate, sodium carbonate, potassium carbonate, lipase, amines, or guanidines.

Still another embodiment of this disclosure is a controlled release fertilizer composition comprising a particulate plant nutrient coated with a coating comprising an isocyanate and a modified polyol, wherein the modified polyol comprises at least one polyhydroxyl compound cross-linked with an unsaturated wax. The modified polyol can include castor oil, vegetable oil based polyols, fatty acids, glyceride mixtures, or unsaturated oleo polyols. Additionally or alternately, the modified polyol can include a mixture of monoglycerides and/or diglycerides formed by reacting a triglyceride and/or diglyceride with any aliphatic, or aromatic, saturated, or unsaturated, natural, or synthetic, liquid, or solid, monofunctional, difunctional, trifunctional, or polyfunctional hydroxyl compound comprising methanol, ethanol, propanol, isopropanol, butanol, isobutanol, pentanol, propenol, propynol, butane diol, butenediol, butynediol, ethylene glycol, diethylene glycol, triethylene glycol, propanediol, dipropylene glycol, polyethylene glycol, polypropylene glycol, trimethylol propane, pentaerythritol, caprolactone polyols, carbonate polyols, ethanolamine, diethanolamine, triethanolamine, tetra (2-hydroxypropyl) ethylenediamine, sorbitol, or simple and/or complex sugars. The modified polyol can be the reaction product of glycerol and the one or more triglycerides reacted in the presence of a catalyst, wherein the catalyst comprises acids, bases organic, inorganic or biologically active compounds including, but not limited to sodium hydroxide, sulfuric acid, sulfonic acid, p-toluene sulfonic acid, metal alkoxides, aluminum isopropoxide, tetraisopropyl titanate, organotin alkoxides, lithium ricinoleate, zinc acetate, sodium carbonate, potassium carbonate, lipase, amines, or guanidines. In some embodiments, the unsaturated wax is one or more vegetable oils, glycerides, partially hydrogenated triglycerides, fatty acids, olefin waxes, silicone waxes, oxidized waxes, natural waxes, natural oils, partially hydrogenated oils or fats.

Yet another embodiment of this disclosure is a controlled release fertilizer composition that has a particulate plant nutrient coated with a coating of an isocyanate and a modified polyol, wherein the modified polyol comprises one or more polyhydroxyl compounds cross-linked to one or more unsaturated waxes and one or more unsaturated triglyceride or triglyceride derivative. The modified polyol can include castor oil, vegetable oil derived polyols, glyceride mixtures, or unsaturated oleo polyols. Additionally or alternately, the modified polyol can include a mixture of monoglycerides and/or diglycerides formed by reacting a triglyceride and/or a diglyceride with any aliphatic or aromatic, saturated or unsaturated, natural or synthetic, liquid or solid, monofunctional, difunctional, trifunctional or polyfunctional hydroxyl compound comprising methanol, ethanol, propanol, isopropanol, butanol, isobutanol, pentanol, propenol, propynol, butane diol, butenediol, butynediol, ethylene glycol, diethylene glycol, triethylene glycol, propanediol, dipropylene glycol, polyethylene glycol, polypropylene glycol, trimethylol propane, pentaerythritol, caprolactone polyols, carbonate polyols, ethanolamine, diethanolamine, triethanolamine, tetra (2-hydroxypropyl)ethylenediamine, sorbitol, or simple and/or complex sugars. The polyol can be the reaction product of glycerol and the one or more triglycerides reacted in the presence of a catalyst, wherein the catalyst comprises acids, bases organic, inorganic or biologically active compounds including, but not limited to sodium hydroxide, sulfuric acid, sulfonic acid, p-toluene sulfonic acid, metal alkoxides, aluminum isopropoxide, tetraisopropyl titanate, organotin alkoxides, lithium ricinoleate, zinc acetate, sodium carbonate, potassium carbonate, lipase, amines, or guanidines.

In still yet another embodiment, this disclosure is to a controlled release fertilizer composition comprising a particulate plant nutrient coated with a coating that includes an isocyanate, 35-99 wt. % castor oil, 0.5-40 wt. % wax and 0.5-25 wt. % sulfur, wherein the sulfur cross-links the castor oil and/or the wax at unsaturated sites in the castor oil and/or wax. In some embodiments, the coating composition has 2-25 wt. % sulfur. In other embodiments, the coating has 40-80 wt. % castor oil, 15-35 wt. % wax and 5-15 wt. % sulfur, or 58-96 wt. % castor oil, 2-25 wt. % wax and 2-17 wt. % sulfur.

In any of the embodiments described above, the plant nutrient includes at least one nutrient from the nutrients listed below at the listed level:

Nitrogen derivatives (as Nitrogen): 0 wt. %-45.54 wt. %
Phosphorus derivatives (as $P_2O_5$): 0 wt. %-51.48 wt. %
Potassium derivatives (as $K_2O$): 0 wt. %-61.38 wt. %
Iron Sulfate: 0 wt. %-99 wt. %
Iron EDTA chelate: 0 wt. %-99 wt. %
Copper Sulfate: 0 wt. %-99 wt. %
Manganese Sulfate: 0 wt. %-99 wt. %
Zinc Sulfate: 0 wt. %-99 wt. %
Sodium Molybdate: 0 wt. %-99 wt. %
Sodium Borate: 0 wt. %-99 wt. %, and/or
Magnesium Sulfate: 0 wt. %-99 wt. %, wherein the listed amounts of nutrients are weight percentages based on the weight of the fertilizer composition.

Additionally or alternately, in any of the embodiments described above, the isocyanate can include any one of a diphenylmethane diisocyanate and/or a toluene diisocyanate including any isomeric, oligomeric, monomeric, or polymeric forms thereof.

Further, in any of the embodiment described above, the modified polyol can be cross-linked with a sulfur, oxygen and/or a peroxide cross-linking moiety. The modified polyol can be cross-linked at unsaturated sites in the modified polyol, unsaturated triglyceride or triglyceride derivative or wax, using heat, UV, or ionizing radiation.

For any of the above described embodiments, the coating can be present in an amount in the range of about 1-20 wt. % based on the weight of plant nutrient, or in the range of about 1-10 wt. %, or even in the range of about 2-4 wt. %.

Additionally, for any of the above described embodiments, a ratio of NCO groups from the isocyanate to the hydroxyl groups in the modified polyol is in the range of about 0.8 to about 3.0, or about 0.8 to about 2.0, or even about 0.8 to about 1.5.

Another embodiment of this disclosure is a process of producing a controlled release fertilizer. The process includes contacting a polyhydroxyl compound with a cross-linking moiety comprising sulfur, oxygen and/or peroxide of up to about 25 wt. % based on the weight of the mixture of the polyhydroxyl compound to provide a modified polyol; contacting a particulate plant nutrient with a mixture comprising the modified polyol and an isocyanate to provide a coated particulate plant nutrient; and curing the coated particulate plant nutrient to provide the controlled release fertilizer. In some embodiments, the cross-linked sulfur, oxygen and/or peroxide moiety is up to about 10 wt. %, or only up to about 5 wt. % based on the weight of the mixture of the polyhydroxyl compound. Yet another embodiment of this disclosure is a process of producing a controlled release fertilizer. The process includes contacting a polyhydroxyl compound with a cross-linking moiety comprising sulfur, oxygen and/or peroxide of up to about 25 wt. % based on the weight of the mixture of the polyhydroxyl compound to provide a modified polyol; contacting a particulate plant nutrient with a mixture comprising the modified polyol, an isocyanate, and wax to provide a coated particulate plant nutrient; and curing the coated particulate plant nutrient to provide the controlled release fertilizer. In some embodiments, the cross-linked sulfur, oxygen and/or peroxide moiety is up to about 10 wt. %, or only up to about 5 wt. % based on the weight of the mixture of the polyhydroxyl compound.

EXAMPLES

Example 1

Cross-linked Castor Oil

In Example 1, different cross-linked castor oil samples were used to prepare controlled release fertilizers. The components used in the various samples are listed in Table 1 below. Sample 1 did not use a cross-linked castor oil, and served as a control sample.

TABLE 1

Castor oil, wax and sulfur compositions

| Description | Polyol mix | | | Catalyst | | Cross-link No/Yes | Mole Ratio |
| | Castor wt. % | Wax wt. % | Sulfur wt. % | Type** | Loading[1] wt. % | | |
| --- | --- | --- | --- | --- | --- | --- | --- |
| Sample 1 (control) | 95 | 5 | 0 | Q | 3.8 | N | 1.2 |
| Sample 2 | 65 | 25 | 10 | T | 3.3 | Y | 1.2 |
| Sample 3 | 70 | 15 | 15 | T | 3.3 | Y | 1.2 |
| Sample 4 | 90 | 5 | 5 | T | 4.5 | Y | 1.2 |
| Sample 5 | 80 | 15 | 5 | T | 4.0 | Y | 1.2 |
| Sample 6* | 87.5 | 0 | 12.5 | T | 4.4 | Y | 1.2 |

Notes
*3.00 mm diameter urea used in sample 6. All other samples used 2.6 mm urea.
**Catalyst used was either QUADROL (Q) or Triethanolamine (T).
[1]Catalyst loading was a weight percent in catalyst plus polyol mix.
In all samples primer used was 0.1 wt. % Triethanolamine and 0.15 wt. % MDI.
"Mole ratio" was the ratio of NCO to OH.
Samples 3, 6: Total coating applied was 3 wt. %.
Samples 1, 2, 4, 5: Total coating applied was 3.25 wt. %.

Sample 1 was the control sample; this sample had no cross-linking. Samples 2, 3, 4, 5 and 6 were inventive examples. In these examples, the samples varied in castor oil loading from 65 wt. % to 90 wt. %, wax loading from 0 wt. % to 25 wt. % and sulfur loading from 5 wt. % to 15 wt. %. The wax used in each of the samples was a $C_{30+}HA$ (alpha olefin wax).

Table 2, below, lists the release data for Samples 1-6.

TABLE 2

Release performance at 20° C. vs. days of exposure for compositions in Table 1

| Days at 20° C. | 1 | 7 | 14 | 21 | 28 | 35 | 42 | 49 |
| --- | --- | --- | --- | --- | --- | --- | --- | --- |
| Sample 1 | 5.0% | 8.2% | 10.4% | 12.2% | 16.8% | 24.0% | 34.9% | 44.9% |
| Sample 2 | 1.4% | 2.9% | 4.3% | 6.4% | 8.2% | 11.5% | 16.3% | 20.7% |
| Sample 3 | 0.6% | 1.1% | 1.4% | 2.7% | 7.2% | 11.8% | 17.8% | 23.2% |
| Sample 4 | 4.3% | 7.5% | 9.7% | 11.5% | 13.7% | 15.5% | 18.5% | 21.4% |
| Sample 5 | 2.1% | 5.0% | 7.9% | 10.1% | 14.1% | 19.2% | 26.6% | 33.4% |
| Sample 6 | 2.1% | 4.3% | 7.8% | 12.2% | 20.2% | 26.1% | 30.6% | 35.2% |

| Days at 20° C. | 56 | 63 | 70 | 77 | 84 | 91 | 98 | 105 |
| --- | --- | --- | --- | --- | --- | --- | --- | --- |
| Sample 1 | 52.7% | 59.0% | 65.0% | 68.6% | 73.1% | 75.6% | 78.4% | |
| Sample 2 | 25.5% | 30.8% | 33.4% | 38.4% | 40.8% | 43.8% | 46.5% | 51.2% |
| Sample 3 | 28.4% | 33.4% | 38.0% | 42.3% | 46.7% | 50.9% | 54.9% | 58.3% |
| Sample 4 | 25.5% | 30.8% | 33.0% | 38.4% | 40.7% | 43.7% | 46.5% | 49.6% |
| Sample 5 | 39.9% | 45.3% | 49.6% | 53.9% | 57.1% | 59.9% | 62.7% | 65.5% |
| Sample 6 | 39.7% | 45.1% | 50.5% | 54.4% | 57.6% | 60.7% | 64.7% | 69.7% |

| Days at 20° C. | 112 | 119 | 126 | 133 | 140 | 147 | 154 | 161 |
| --- | --- | --- | --- | --- | --- | --- | --- | --- |
| Sample 1 | | | | | | | | |
| Sample 2 | 52.3% | 55.5% | 57.5% | 60.3% | 62.3% | 65.1% | 66.3% | 68.3% |

TABLE 2-continued

| Release performance at 20° C. vs. days of exposure for compositions in Table 1 | | | | | | | |
|---|---|---|---|---|---|---|---|
| Sample 3 | 61.4% | 64.2% | 67.0% | 69.3% | 71.4% | 73.5% | 75.4% |
| Sample 4 | 51.9% | 55.1% | 57.4% | 60.2% | 62.2% | 63.8% | 66.2% | 68.2% |
| Sample 5 | 70.3% | 71.5% | 73.2% | 75.6% | | | |
| Sample 6 | 72.8% | 75.2% | 80.2% | | | | |

Sample 1 exhibited 80% release at 98 days. In contrast, Samples 2-6 exhibited a 40% to 65% nutrient release by the 98$^{th}$ day, which is indicative of a much longer lasting controlled release fertilizer. Release studies were terminated after 161 days. At that point, some of the compositions (e.g. Samples 2 and 4) were still exhibiting nutrient release.

Example 2

Cross-Linked Castor Oil

In Example 2, different cross-linked castor oil samples were used to prepare controlled release fertilizers. The components used in the various samples are listed in Table 3.

TABLE 3

| | Composition of samples with several possible variations | | | | | |
|---|---|---|---|---|---|---|
| | Polyol Mix | | | | Cross-linking variables | |
| | Castor | Wax wt. % | | Sulfur | | Temp. | Time |
| Description | wt. % | Veg. Oil | Olefin wax | wt. % | No/Yes | (° C.) | (min) |
| Sample 7a | 65 | 12.5[1] | 12.5 | 10 | N | | |
| Sample 7b | 65 | 12.5[1] | 12.5 | 10 | Y | 165 | 35 |
| Sample 8 | 65 | 15.0[2] | 10 | 10 | Y | 165 | 40 |
| Sample 9 | 65 | 25.0[3] | 0 | 10 | Y | 165 | 60 |
| Sample 10 | 65 | 25.0[1] | 0 | 10 | Y | 165 | 60 |
| Sample 11 | 65 | 0 | 25 | 10 | Y | 180 | 10 |
| Sample 12[4] | 55 | 0 | 25 | 20 | Y | 140 | 60 |
| Sample 13 | 70 | 0 | 20[5] | 10 | Y | 165 | 60 |

Notes

[1] Boiled Linseed oil

[2] Tall oil fatty acid

[3] Partially hydrogenated soybean oil

[4] 1 wt. % Zinc oxide, 1 wt. % stearic acid, 0.6 wt. % tetramethylthiuram disulfide (TMTD), 0.3 wt. % dibenzylthiazyl disulfide (MBTS)

[5] $C_{20-24}$ Alpha olefin wax

Samples 7a and 7b were both prepared using linseed oil and serve as a comparison to highlight that cross-linking is advantageous. Vegetable oils such as linseed oil have double bonds that allow them to participate in the sulfur cross-linking reaction, however, since they do not have —OH functionality, they cannot participate in the urethane reaction.

Sample 8 was prepared using a tall oil fatty acid (unsaturated fatty acid such). Sample 8 was used to demonstrate that tri-glycerides such as, for example vegetable oils, mixtures of mono/di glycerides and/or fatty acids can be an effective complementary, substitute to participate in the sulfur cross-linking reaction along with cross-linkable waxes.

Sample 9 included partially hydrogenated soybean oil. Sample 10 included linseed oil. Samples 9 and 10 demonstrated that a cross-linkable wax is not a required ingredient.

Sample 11 demonstrated that the cross-linking reaction can be carried out at a different combination of temperature and time. For example, the cross-linking reaction was carried out at 180° C. for 10 min.

Sample 12 demonstrated that accelerators known in the literature can be used to influence the rate of cross-linking reaction. The reaction used to produce Sample 12 was carried out a lower temperature (140° C.). Sample 12 had a loading of 20 wt % sulfur.

Sample 13 demonstrated that a different olefin wax can be used instead of $C_{30+}$HA wax. A $C_{20-24}$ alpha olefin wax was used in the preparation of Sample 13.

TABLE 4

Release performance at 20° C. vs, days of exposure for compositions in Table 3

| Days at 20° C. | 1 | 7 | 14 | 21 | 28 | 35 | 42 | 49 |
|---|---|---|---|---|---|---|---|---|
| Sample 7a | 1.4% | 10.8% | 40.0% | 61.2% | 72.5% | 80.7% | | |
| Sample 7b | 1.4% | 4.3% | 6.5% | 7.9% | 10.1% | 13.0% | 18.9% | 25.6% |
| Sample 8 | 5.0% | 8.6% | 10.8% | 12.3% | 13.7% | 15.9% | 18.1% | 19.6% |
| Sample 9 | 2.1% | 4.3% | 10.8% | 18.9% | 27.1% | 35.4% | 43.1% | 49.3% |
| Sample 10 | 9.4% | 15.2% | 19.6% | 28.6% | 39.2% | 48.5% | 55.6% | 61.2% |
| Sample 11 | 1.8% | 2.5% | 3.2% | 3.2% | 4.5% | 5.4% | 6.8% | 8.6% |
| Sample 12 | 2.1% | 4.3% | 7.2% | 11.5% | 14.5% | 18.9% | 24.1% | 28.6% |
| Sample 13 | 3.6% | 7.9% | 11.5% | 14.4% | 18.8% | 22.5% | 28.5% | 33.1% |

| Days at 20° C. | 56 | 63 | 70 | 77 | 84 | 91 | 98 | 105 |
|---|---|---|---|---|---|---|---|---|
| Sample 7a | | | | | | | | |
| Sample 7b | 33.9% | 40.0% | 45.4% | 49.3% | | | | |
| Sample 8 | 21.8% | 24.8% | 30.1% | 34.6% | | | | |
| Sample 9 | 54.8% | 59.6% | 63.6% | 66.8% | | | | |
| Sample 10 | 66.0% | 70.1% | 73.3% | 76.6% | | | | |
| Sample 11 | 10.4% | 13.3% | 17.0% | 19.6% | 22.9% | 25.5% | 28.5% | 31.5% |
| Sample 12 | 32.4% | 36.2% | 40.0% | 43.9% | 47.8% | 50.9% | | |
| Sample 13 | 39.2% | 41.5% | 44.5% | 48.0% | 52.9% | 56.3% | 59.5% | 62.7% |

Sample 7a exhibited 80% release in 35 days, while Sample 7b exhibited a much longer release life (50% released by 77 days).

Samples 8-13 all had release lives comparable to or exceeding the release life of control Sample 1 (Example 1).

TABLE 5

| | Viscosity (η) Data | | | |
|---|---|---|---|---|
| | Polyol mix | | | Relative Viscosity at |
| Sample No | Castor wt. % | Wax wt. % | Sulfur wt. % | 80° C. $\eta_{x\text{-linked mix}}/\eta_{castor}$ |
| 1 | 75.0 | 25.0 | 0.0 | 0.7 |
| 2 | 75.0 | 0.0 | 25.0 | 85.8 |
| 3 | 75.0 | 25.0 | 0.0 | 0.8 |
| 4 | 70.8 | 19.0 | 10.3 | 1.7 |
| 5 | 82.0 | 0.0 | 18.0 | 16.8 |
| 6 | 87.5 | 0.0 | 12.5 | 6.4 |
| 7 | 70.8 | 10.3 | 19.0 | 8.6 |
| 8 | 83.3 | 8.3 | 8.3 | 2.7 |
| 9 | 60.0 | 15.0 | 25.0 | 23.0 |
| 10 | 100.0 | 0.0 | 0.0 | 1.0 |
| 11 | 60.0 | 15.0 | 25.0 | 59.6 |
| 12 | 60.0 | 25.0 | 15.0 | 3.7 |
| 13 | 100.0 | 0.0 | 0.0 | 1.0 |
| 14 | 87.5 | 12.5 | 0.0 | 1.0 |

In a mixture design of experiments, several compositions, including replicates, were prepared and the viscosity was measured at 80° C. The viscosity measurements for the cross-linked mixture were normalized with the viscosity of pure castor oil and the normalized values are reported in the above table.

The release rate of controlled release fertilizer compositions including castor oil cross-linked with sulfur was investigated. Additionally, the effect of the addition of a triethanolamine (TEA) primer on the release rate of CRF compositions was also studied. It was determined that cross-linking castor oil with sulfur had a positive effect.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. A controlled release fertilizer composition comprising a particulate plant nutrient coated with a polyurethane coating comprising an isocyanate and a modified polyol, wherein the modified polyol comprises about 35-99 wt. % castor oil, about 0.5-40 wt. % wax and about 0.5-25 wt. % sulfur, wherein the sulfur cross-links the castor oil and/or wax at unsaturated sites in the castor oil and/or wax.

2. The controlled release fertilizer of claim 1, wherein the modified polyol further comprises vegetable oil derived polyols, glyceride mixtures, or unsaturated oleo polyols.

3. The controlled release fertilizer of claim 1, wherein the modified polyol further comprises one or more polyhydroxyl compound cross-linked with an unsaturated glyceride or glyceride derivative.

4. The controlled release fertilizer of claim 1, wherein the plant nutrient comprises at least one nutrient from the nutrients listed below:
   Nitrogen derivatives (as Nitrogen): 0 wt. %-45.54 wt. %
   Phosphorus derivatives (as $P_2O_5$): 0 wt. %-51.48 wt. %
   Potassium derivatives (as $K_2O$): 0 wt. %-61.38 wt. %
   Iron Sulfate: 0 wt. %-99 wt. %
   Iron EDTA chelate: 0 wt. %-99 wt. %
   Copper Sulfate: 0 wt. %-99 wt. %
   Manganese Sulfate: 0 wt. %-99 wt. %
   Zinc Sulfate: 0 wt. %-99 wt. %
   Sodium Molybdate: 0 wt. %-99 wt. %
   Sodium Borate: 0 wt. %-99 wt. %, and/or
   Magnesium Sulfate: 0 wt. %-99 wt. %, wherein the listed amounts of nutrients are weight percentages based on the weight of the fertilizer composition.

5. The controlled release fertilizer of claim 1, wherein the isocyanate comprises any one of a diphenylmethane diisocyanate and/or a toluene diisocyanate including any isomeric, oligomeric, monomeric, or polymeric forms thereof.

6. The controlled release fertilizer of claim 1, wherein the wax is one or more vegetable oils, glycerides, partially hydrogenated glycerides, fatty acids, olefin waxes, silicone waxes, oxidized waxes, natural waxes, natural oils, partially hydrogenated oils or fats.

7. The controlled release fertilizer of claim 1, comprising 58-96 wt. % castor oil, 2-25 wt. % wax and 2-17 wt. % sulfur.

* * * * *